United States Patent
Harada et al.

(10) Patent No.: US 10,123,394 B2
(45) Date of Patent: Nov. 6, 2018

(54) CONTROL METHOD OF INFORMATION TERMINAL APPARATUS PROVIDED WITH VIBRATION SENSOR

(71) Applicant: Panasonic Intellectual Property Management Co., Ltd., Osaka (JP)

(72) Inventors: Masaaki Harada, Osaka (JP); Kozo Nishimura, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 3 days.

(21) Appl. No.: 15/427,052

(22) Filed: Feb. 8, 2017

(65) Prior Publication Data

US 2017/0257929 A1    Sep. 7, 2017

(30) Foreign Application Priority Data

Mar. 3, 2016 (JP) .................................. 2016-041528

(51) Int. Cl.
| | |
|---|---|
| *A61B 5/11* | (2006.01) |
| *H05B 37/02* | (2006.01) |
| *G01H 1/00* | (2006.01) |
| *G08C 17/00* | (2006.01) |

(52) U.S. Cl.
CPC ........ *H05B 37/0227* (2013.01); *A61B 5/1116* (2013.01); *A61B 5/1123* (2013.01); *G01H 1/00* (2013.01); *G08C 17/00* (2013.01); *G08C 2200/00* (2013.01)

(58) Field of Classification Search
CPC ....... A61B 5/0051; A61B 5/11; A61B 5/1123; A61B 5/4806; A61B 5/6892; A61B 5/7203; A61B 5/7282

USPC .................................................. 600/534, 552
See application file for complete search history.

(56) References Cited

U.S. PATENT DOCUMENTS

| | | | | |
|---|---|---|---|---|
| 7,290,451 | B2 * | 11/2007 | Taniguchi ................ | A61B 5/11 73/599 |
| 7,630,537 | B2 * | 12/2009 | Sato ...................... | A61B 5/0064 250/574 |
| 8,403,865 | B2 * | 3/2013 | Halperin ................ | A61B 5/113 600/529 |
| 8,491,492 | B2 * | 7/2013 | Shinar ................... | A61B 5/0205 600/16 |
| 2004/0082874 | A1 * | 4/2004 | Aoki .................... | A61B 5/1135 600/534 |

(Continued)

FOREIGN PATENT DOCUMENTS

JP    2006-181263    7/2006

*Primary Examiner* — Tung X Le

(74) *Attorney, Agent, or Firm* — Greenblum & Bernstein, P.L.C.

(57) ABSTRACT

In a control method, a vibration sensor of an information terminal apparatus acquires vibration data that is time-sequential data of vibrations including vibrations based upon body movements of a user on bedding on which the information terminal apparatus is placed. The acquired vibration data is stored in a memory, an action performed by the user is detected, and, from among the vibration data stored in the memory, vibration data included in a predetermined period that ends at a time at which the detected action was performed is extracted. Then, a vibration waveform indicated by the extracted vibration data is stored in the memory as a bed-leaving vibration pattern produced by the user.

9 Claims, 12 Drawing Sheets

(56) References Cited

U.S. PATENT DOCUMENTS

2014/0229017 A1* 8/2014 Oyama .............. G05D 23/1905
  700/276
2016/0150980 A1* 6/2016 Lee .......................... A61B 6/12
  600/484

* cited by examiner

| TIME | DEVICE NAME | OPERATION CONTENT |
|---|---|---|
| 1/1/2001 2:30 | BATHROOM LIGHT | ON |
| 1/1/2001 2:35 | BATHROOM LIGHT | OFF |
| ... | ... | ... |

CONTROL METHOD OF INFORMATION TERMINAL APPARATUS PROVIDED WITH VIBRATION SENSOR

BACKGROUND

1. Technical Field

The present disclosure relates to a control method of an information terminal apparatus provided with a vibration sensor, to a body movement measuring apparatus, and to a recording medium.

2. Description of the Related Art

To date, body movement measuring devices have been disclosed that monitor the sleep state of a sleeping person in order to comprehend the health condition of the sleeping person and so forth.

For example, in the body movement measuring apparatus disclosed in Japanese Patent No. 4329690, a sensor is installed in bedding and used to capture the lowest values of sensor values in real time, fluctuations in the lowest values of the sensor values are lessened by means of an exponential function to obtain a value that is set as a body movement determination threshold value, rough movement signals and slight movement signals are thereby separated, and the sleep state of a sleeping person is determined. It is indicated that this body movement measuring device is able to determine the sleep of a sleeping person in a highly precise manner irrespective of the type and state of bedding and the body weight of the sleeping person. Here, a rough movement signal is a signal derived from a movement or the like of the body of the sleeping person such as falling asleep, leaving bed, and turning over in bed, and a slight movement signal is a signal derived from the respiration and heart rate of the sleeping person.

Furthermore, in the body movement measuring apparatus disclosed in Japanese Patent No. 4329690, it is indicated that an upper limit signal level is provided which is greater than the body movement determination threshold value and a set multiple of the body movement determination threshold value, the body movement determination threshold value is updated on the basis of vibration data that is equal to or less than the upper limit signal level, and it is thereby possible to suppress an increase in the body movement determination threshold value in the case where a sleeping person has clearly caused a rough movement.

SUMMARY

However, further investigation is required in order to determine movements of a user with greater precision by means of a body movement measuring apparatus.

In one general aspect, the techniques disclosed here feature a method that includes: acquiring, using a vibration sensor of an information terminal apparatus, vibration data that is time-sequential data of vibrations, including vibrations based upon body movements of a user on bedding on which the information terminal apparatus is placed; storing the acquired vibration data in a memory of the information terminal apparatus; detecting an action performed by the user; and extracting, from among the vibration data stored in the memory, vibration data included in a predetermined period that ends at a time at which the detected action was performed, and storing a vibration waveform indicated by the extracted vibration data, in the memory as a bed-leaving vibration pattern produced by the user.

It should be noted that general or specific aspects hereof may be realized by a system, a method, an integrated circuit, a computer program, or a recording medium such as a computer-readable CD-ROM, and may be realized by an arbitrary combination of a system, a method, an integrated circuit, a computer program, and a recording medium.

According to the aforementioned aspect, further improvement can be realized.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

Figure 1:
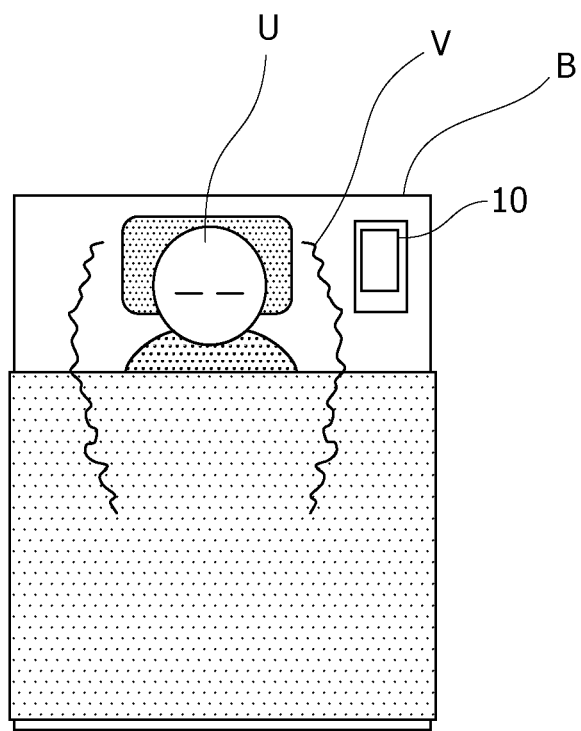
FIG. 1 is a conceptual diagram depicting a mode of use of an information terminal apparatus in an embodiment.

DETAILED DESCRIPTION (Findings Forming the Basis for the Present Disclosure)

In recent years, it has been said that sleeping time has decreased due to changes in daily living habits in Japan, and that the level of satisfaction with sleep has declined. The sleep measuring apparatus and so forth disclosed in Japanese Patent No. 4329690 have been developed from the need that users wish to comprehend their own sleep states. However, to use the sleep measuring apparatus disclosed in Japanese Patent No. 4329690, it is necessary for a special sensor to be separately purchased and attached to bedding, and it is difficult for the sleep measuring apparatus to be easily used from the aspects of cost and installation work.

Furthermore, when consideration is given to applying the body movement measuring method disclosed in Japanese Patent No. 4329690 to a body movement measuring apparatus that uses a vibration sensor such as an acceleration sensor or gyro sensor housed within a general information terminal apparatus (a smartphone, a mobile telephone terminal, or the like), the measurement precision of the sensor of the body movement measuring apparatus disclosed in Japanese Patent No. 4329690 is high, and it is therefore possible for fluctuations in the lowest values of the sensor that indicate slight movement signals of a subject to be monitored and thereby separated from rough movement signals. However, with a body movement measurement performed by an information terminal apparatus, there is variation in acquired sensor values due to differences in sensor sensitivity owing to the model of the information terminal apparatus, differences in bedding due to the information terminal apparatus being placed on bedding to measure body movements of the subject, and so forth. The sensor values acquired by the vibration sensor of the information terminal apparatus include variations in the sensor values caused by factors such as the aforementioned, and it is therefore not possible to capture slight movement signals of the subject on the basis of fluctuations in the lowest values of the sensor. Consequently, the body movement measuring method disclosed in Japanese Patent No. 4329690 is not suitable for a body movement measuring apparatus that uses the aforementioned vibration sensor of the information terminal apparatus. Thus, for this kind of body movement measuring apparatus, there is no choice but to adopt a method in which the body movement determination threshold value is determined on the basis of fluctuations in slight movement signals having large amplitude values from among vibration data.

In addition, in the body movement measuring apparatus disclosed in Japanese Patent No. 4329690, an upper limit signal level that is a set multiple of the body movement determination threshold value is provided, and it is thereby possible to suppress, to an extent, the body movement determination threshold value being set high due to rough movements of a sleeping person; however, depending on the setting of the multiple, it may not be possible to remove rough movement signals having a signal level the removal of which is desirable. Thus, it is possible that the precision of determining body movements or movements of the user may decline with the aforementioned body movement measuring apparatus.

It is desirable to provide a body movement measuring apparatus that is able to solve these problems and to also easily determine body movements or movements of the user in a highly precise manner with only a general information terminal apparatus having a vibration sensor mounted therein owned by the user. To date, technical solutions for satisfying these demands have not been investigated.

In order to solve these kinds of problems, a method according to an aspect of the present disclosure includes: acquiring, using a vibration sensor of an information terminal apparatus, vibration data that is time-sequential data of vibrations, including vibrations based upon body movements of a user on bedding on which the information terminal apparatus is placed; storing the acquired vibration data in a memory of the information terminal apparatus; detecting an action performed by the user; and extracting, from among the vibration data stored in the memory, vibration data included in a predetermined period that ends at a time at which the detected action was performed, and storing a vibration waveform indicated by the extracted vibration data, in the memory as a bed-leaving vibration pattern produced by the user.

According to the aforementioned aspect, the information terminal apparatus generates the bed-leaving vibration pattern on the basis of the body movements of the user in the bedding actually being used by the user in a predetermined period before the time at which the user performed the action. In this way, because the vibration pattern is generated on the basis of vibrations in the bedding actually being used, it is possible to more precisely determine a body movement of the user in this bedding, using this generated vibration pattern. Thus, the information terminal apparatus is able to determine movements of the user with greater precision.

For example, the method further includes: determining whether or not the vibration waveform indicated by the acquired vibration data conforms with the vibration pattern stored in the memory; and, when having determined that the vibration waveform indicated by the acquired vibration data conforms with the vibration pattern, transmitting, via a network, a control signal that causes operation of an electrical device that can be controlled by the information terminal apparatus via the network.

According to the aforementioned aspect, the information terminal apparatus is able to control the electrical device when it has been determined that the user has left bed on the basis of the generated vibration pattern. Thus, when the user has left bed, it is possible for the information terminal apparatus to determine that the user has left bed and automatically control the electrical device, thereby improving convenience.

For example, the method further includes: acquiring log information that includes a time at which an operation by the user was performed with respect to the electrical device, in which, when the action performed by the user is to be detected, the action performed by the user is detected on the basis of the acquired log information, and, when the vibration pattern is to be stored in the memory, the vibration pattern is stored in the memory with the time included in the acquired log information being used as the time at which the action was performed.

According to the aforementioned aspect, the information terminal apparatus generates the bed-leaving vibration pattern of the user with the time at which the user operated the electrical device serving as the time at which the user performed the action. In this way, the information terminal apparatus is able to specifically determine movements of the user with greater precision.

For example, the method further includes: acquiring log information that includes a time at which an operation by the user was performed with respect to the information terminal apparatus, in which, when the action performed by the user is to be detected, the action performed by the user is detected on the basis of the acquired log information, and, when the vibration pattern is to be stored in the memory, the vibration pattern is stored in the memory with the time included in the acquired log information being used as the time at which the action was performed.

According to the aforementioned aspect, the information terminal apparatus generates the bed-leaving vibration pattern of the user with the time at which the user operated the information terminal apparatus serving as the time at which the user performed the action. In this way, the information terminal apparatus is able to specifically determine movements of the user with greater precision.

For example, the method further includes: acquiring a detection result produced by a person-detecting sensor capable of detecting that the user is in a location that is different from on the bedding, in which, when the action performed by the user is to be detected, the action performed by the user is detected on the basis of the acquired detection result, and, when the vibration pattern is to be stored in the memory, the vibration pattern is stored in the memory with a time included in the acquired detection result being used as the time at which the action was performed.

According to the aforementioned aspect, the information terminal apparatus generates the bed-leaving vibration pattern of the user with the time at which the user was detected by the person-detecting sensor serving as the time at which the user performed the action. In this way, the information terminal apparatus is able to specifically determine movements of the user with greater precision.

For example, in the method, when the vibration pattern is to be stored in the memory, the vibration pattern is generated by machine learning with the vibration waveform indicated by the extracted vibration data serving as teacher data, and the generated vibration pattern is stored in the memory.

According to the aforementioned aspect, the information terminal apparatus generates the bed-leaving vibration pattern of the user by means of machine learning. In this way, the information terminal apparatus generates the vibration pattern by means of machine learning on the basis of vibrations in the bedding actually being used, and is therefore able to more precisely determine a body movement of the user in this bedding.

For example, in the method, generation of the vibration pattern by machine learning is performed only in a period determined as being a period in which a vibration pattern based upon the body movements of the user is to be learned.

According to the aforementioned aspect, the information terminal apparatus no longer performs machine learning when a vibration pattern learning period has ended, and therefore there is an advantage in that the processing load is reduced.

Furthermore, a body movement measuring apparatus according to an aspect of the present disclosure is provided with: a vibration sensor capable of detecting vibrations of the body movement measuring apparatus; a memory; a processor; and a medium having a computer program stored thereon, the computer program causing the processor to execute operations including: acquiring vibration data that is time-sequential data of the vibrations detected by the vibration sensor, including vibrations based upon body movements of a user on bedding on which the body movement measuring apparatus is placed, and storing the acquired vibration data in the memory; detecting an action performed by the user; and extracting, from among the vibration data stored in the memory, vibration data included in a predetermined period that ends at a time at which the detected action was performed, and storing a vibration waveform indicated by the extracted vibration data, in the memory as a bed-leaving vibration pattern produced by the user.

According to the aforementioned aspect, the body movement measuring apparatus demonstrates an effect that is similar to that of the aforementioned method.

Furthermore, a program according to an aspect of the present disclosure is a program for causing a computer to execute the method described above.

According to the aforementioned aspect, the program demonstrates an effect that is similar to that of the aforementioned method.

It should be noted that general or specific aspects hereof may be realized by a system, a method, an integrated circuit, a computer program, or a recording medium such as a computer-readable CD-ROM, and may be realized by an arbitrary combination of a system, a method, an integrated circuit, a computer program, or a recording medium.

Hereinafter, embodiments will be described in a specific manner with reference to the drawings.

It should be noted that the embodiments described hereinafter all represent general or specific examples. The numerical values, the shapes, the materials, the constituent elements, the arrangement positions and modes of connection of the constituent elements, the steps, and the order of the steps and the like given in the following embodiments are examples and are not intended to limit the present disclosure. Furthermore, from among the constituent elements in the following embodiments, constituent elements that are not mentioned in the independent claims indicating the most significant concepts are described as optional constituent elements.

Embodiment

In the present embodiment, a body movement measuring apparatus that determines movements of a user with greater precision will be described. The body movement measuring apparatus may have a hardware configuration that is the same as a general information terminal apparatus (a smartphone, a mobile telephone terminal, or the like) that is provided with a vibration sensor, or may be a dedicated device (also referred to as a body movement measuring apparatus) that is provided with a general vibration sensor. Hereinafter, as an example, a case where the body movement measuring apparatus is realized by an information terminal apparatus will be described.

Figure 2:
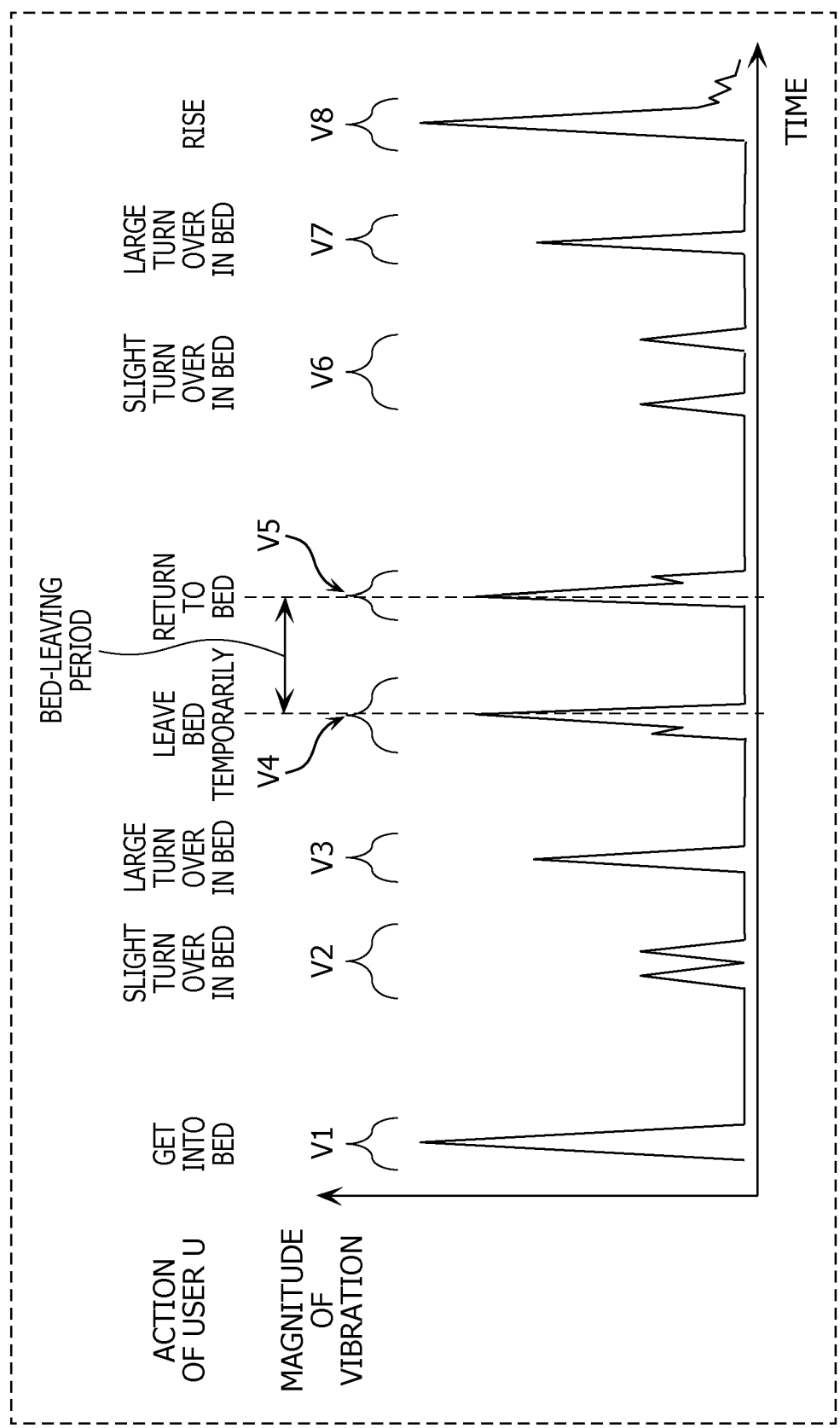
FIG. 2 is an explanatory diagram depicting a relationship between the magnitude of vibrations detected by the information terminal apparatus and actions performed by a user in the embodiment.

FIG. 1 is a conceptual diagram depicting a mode of use of an information terminal apparatus 10 in the present embodiment. FIG. 2 is an explanatory diagram depicting a relationship between the magnitude of vibrations detected by the information terminal apparatus 10 and actions of the user U in the present embodiment.

As depicted in FIG. 1, the information terminal apparatus 10 is placed on bedding B of the user U. When the body of the user U moves, the information terminal apparatus 10 vibrates due to vibrations V of the bedding B that occur together with the movement of the body of the user U. The information terminal apparatus 10 is provided with a vibration sensor, and, when the information terminal apparatus 10 vibrates due to the vibrations V of the bedding B, the vibration sensor detects vibrations of the information terminal apparatus 10. In this way, the information terminal apparatus 10 detects whether or not there is a body movement of the user U and the magnitude of the body movement on the basis of the vibrations of the information terminal apparatus 10.

Here, the vibrations V propagate from the body of the user U, through the bedding B, and reach the information terminal apparatus 10. The way in which the vibrations V propagate differs depending on the type of bedding B (the material, weight, hardness, and the like of the contents thereof), the type of placement surface (the material, hardness, and the like) on which the bedding B has been placed, and so forth. Thus, the magnitude of the vibrations detected by the information terminal apparatus 10 are different when the bedding B is different or when the placement location or placement surface of the bedding B is different, even when the body movements by the user U have been the same.

Hence, it is necessary for the information terminal apparatus 10 to measure body movements of the user U in an appropriate manner, in accordance with the actual placement location or placement surface of the bedding B.

Movements of the body of the user U include comparatively small movements produced by movements of the body made during sleep such as the user U turning over in bed, and comparatively large movements produced by the user U leaving bed or getting into bed. The information terminal apparatus 10, by means of machine learning, generates determination criteria for determining whether the user U is asleep or has left bed, on the basis of features such as the magnitude of detected vibrations. Then, when it has been determined that the user U has left bed on the basis of the generated determination criteria, the control of another electrical device is performed, for example. For instance, when the information terminal apparatus 10 has detected that the user U has left bed, control can be performed such as turning on air conditioning control of an air conditioner in the room in which the bedding B has been set up, on the basis of the detection result.

For example, as depicted in FIG. 2, the information terminal apparatus 10 detects a plurality of vibrations V1 to V8 that are based upon movements of the body of the user U, during a period from the user U getting into bed to rising. Then, on the basis of vibration waveforms, the information terminal apparatus 10 determines that, from among these vibrations V1 to V8, a vibration V4 produced when temporarily leaving bed and a vibration V8 produced when rising are due to the user U leaving bed, and performs control to turn on a light in the bedroom at a predetermined brightness, output music at a predetermined volume, or turn on a light in a bathroom and a corridor leading to the bathroom. It should be noted that temporarily leaving bed is one example of leaving bed, and refers to when the user U leaves bed and then gets into bed once again (also referred to as returning to bed) before rising. Furthermore, rising is one example of leaving bed, and refers to leaving bed when the user U finishes sleeping and awakens.

The configuration of the information terminal apparatus 10 and processing executed by the information terminal apparatus 10 will be described in detail hereinafter.

Figure 3:
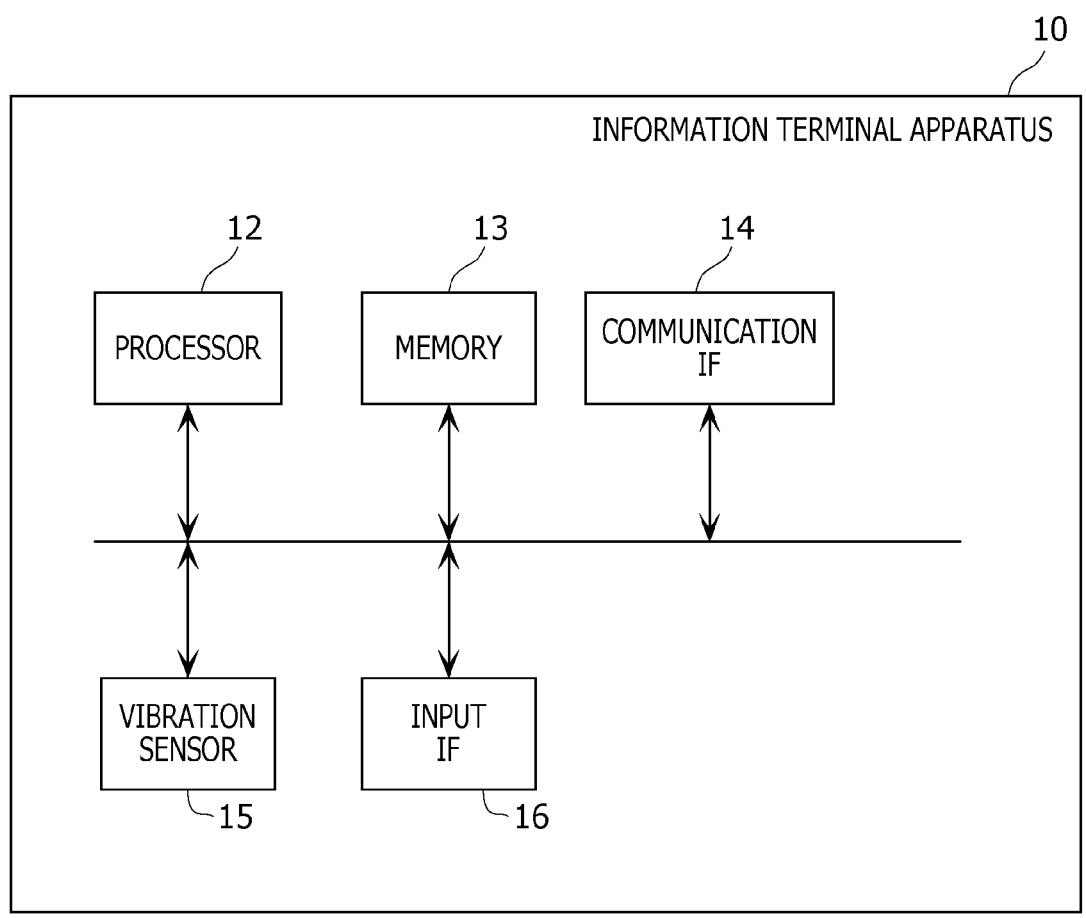
FIG. 3 is a block diagram depicting a hardware configuration of the information terminal apparatus in the embodiment.

FIG. 3 is a block diagram depicting a hardware configuration of the information terminal apparatus 10 in the present embodiment.

As depicted in FIG. 3, the information terminal apparatus 10 is provided with a processor 12, a memory 13, a communication interface (IF) 14, a vibration sensor 15, and an input IF 16.

The processor 12 is a processor that executes a control program stored in the memory 13 or the like. Processing executed by the information terminal apparatus 10 can be realized by the processor 12 executing the control program.

The memory 13 is a storage device that stores information, and has a volatile storage area that is used as a work area to be used when the processor 12 executes the control program, and a nonvolatile storage area in which the control program, data, and the like are stored.

The communication IF 14 is a communication interface that is connected to a network, and is for communicating with an external communication device by way of the network. The communication IF 14 is used when the information terminal apparatus 10 implements a telephone call, an electronic mail, or Internet access either on the basis of an operation performed by the user U or automatically. The communication IF 14, for example, is realized by means of a mobile telephone communication interface (for example, a 3.5 generation mobile telecommunications system (3.5G) or a 3.9 generation mobile telecommunications system (3.9G)), a wired local area network (LAN) (for example, a wired LAN conforming with the IEEE 802.3 specification or Ethernet (registered trademark)), or a wireless LAN (for example, IEEE 802.11a, b, g, or n).

The vibration sensor 15 is a vibration sensor that detects vibrations of the information terminal apparatus 10, and outputs vibration data that indicates the magnitude of the detected vibrations. Specifically, the vibration sensor 15 has at least one of an acceleration sensor that detects acceleration, a gyro sensor that detects angular velocity, and an angle sensor that detects an angle formed with a reference angle, for example. It should be noted that the aforementioned vibrations include not only vibrations serving as periodic movements centered on one location, but also physical quantities that can be acquired by the aforementioned sensor, such as changes in location or changes in angle, for example.

The input IF 16 is an input interface that receives operations by the user U. The input IF 16, for example, is a touch panel, a touch pad, or a button, or, more specifically, is a touch panel portion of a touch panel display.

Figures 4, 5:
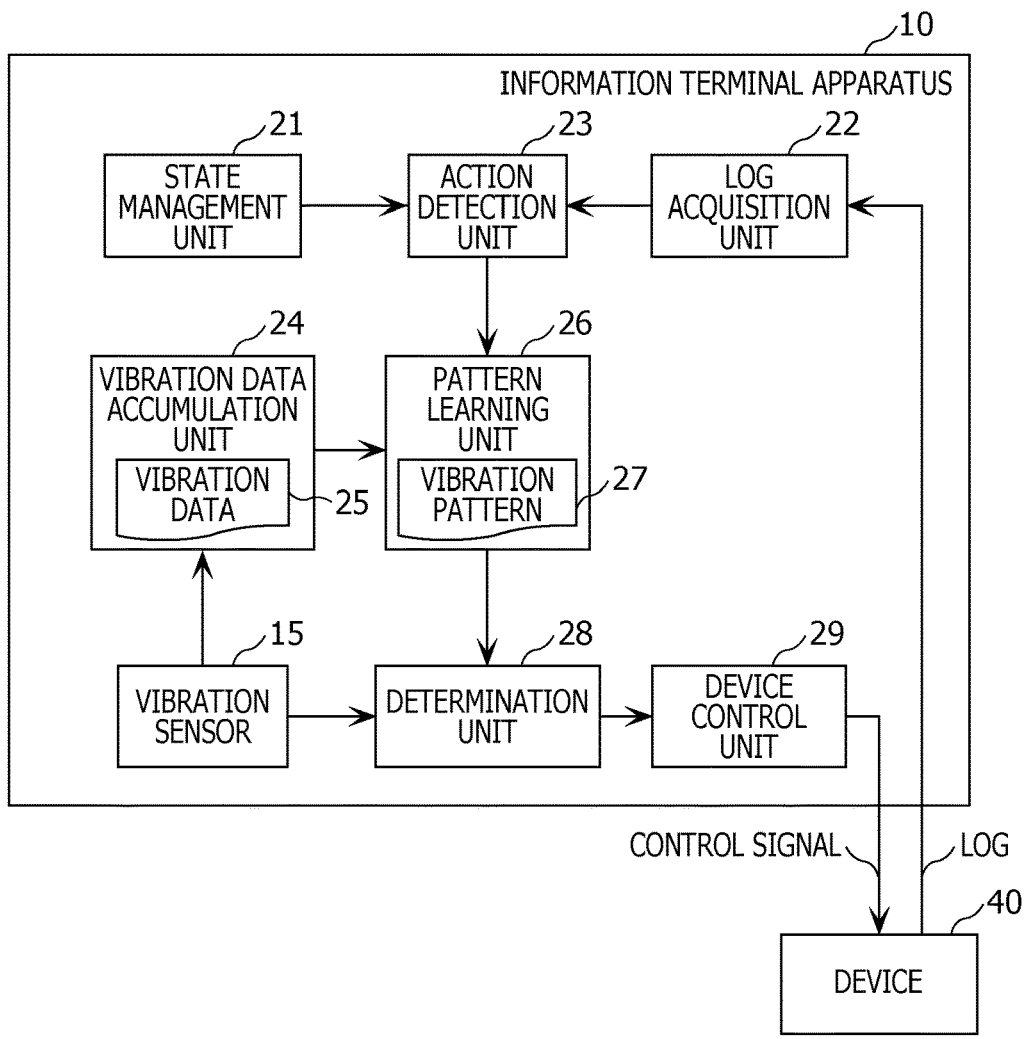
FIG. 4 is a block diagram depicting a functional configuration of the information terminal apparatus in the embodiment.
FIG. 5 is an explanatory diagram depicting an example of a log of a device in the embodiment.

FIG. 4 is a block diagram depicting a functional configuration of the information terminal apparatus 10 in the present embodiment.

As depicted in FIG. 4, the information terminal apparatus 10 is provided with a state management unit 21, a log acquisition unit 22, an action detection unit 23, a vibration data accumulation unit 24, a pattern learning unit 26, a determination unit 28, and a device control unit 29. Furthermore, a device 40 that is an electrical device is communicably connected via the network to the information terminal apparatus 10.

It should be noted that the aforementioned constituent elements may be logical function blocks realized by the processor 12 executing a program, or may be physical function blocks configured by means of dedicated circuits. It should be noted that the vibration sensor 15 depicted in FIG. 4 is the vibration sensor 15 depicted in FIG. 3.

The state management unit 21 is a processing unit that manages which state the information terminal apparatus 10 is to enter, from among a plurality of predetermined states. The plurality of predetermined states include at least a first state, a second state, and a stopped state.

The first state refers to a state in which the information terminal apparatus 10 detects actions of the user U, and performs a bed-leaving determination with regard to the user U. The first state can be used in a period in which machine learning is performed with regard to vibration waveforms produced by body movements of the user U, in order for the information terminal apparatus 10 to appropriately detect the user U leaving bed.

The second state refers to a state in which the information terminal apparatus 10 performs a bed-leaving determination with regard to the user U without detecting actions of the user U. The second state can be used in a period in which, after the machine learning in the first state has been completed, the vibration waveforms generated by the learning are used to detect the user U leaving bed.

The stopped state refers to a state in which the information terminal apparatus 10 does not detect actions or even perform a bed-leaving determination with regard to the user U. The stopped state can be used in a period in which the user U leaving bed is not detected (for example, when the user U is awake and active during the day), or the like.

The state management unit 21 decides which of the aforementioned states the information terminal apparatus 10 is to enter, on the basis of operations by the user U received by the input IF 16 and other conditions. The state management unit 21 controls which of the aforementioned three states the information terminal apparatus 10 is to enter, by controlling whether or not the action detection unit 23 and the determination unit 28 are to be made to operate. Specifically, the information terminal apparatus 10 enters the first state when the state management unit 21 causes both the action detection unit 23 and the determination unit 28 to operate. Furthermore, the information terminal apparatus 10 enters the second state when the state management unit 21 does not cause the action detection unit 23 to operate and causes the determination unit 28 to operate. Furthermore, the information terminal apparatus 10 enters the stopped state when the state management unit 21 does not cause either of the action detection unit 23 or the determination unit 28 to operate.

The state management unit 21, for example, may manage states in such a way that the information terminal apparatus 10 enters the first state when a bed-leaving vibration pattern of the user U has not yet been generated. Furthermore, the state management unit 21 may manage states in such a way that the information terminal apparatus 10 enters the second state after having operated in the first state for approximately one week or one month. In this way, a vibration pattern may be generated by means of machine learning only in a period determined as being a period in which vibration patterns based upon body movements of the user U are to be learned.

The log acquisition unit 22 is a processing unit that acquires information (also referred to as log information or simply a log) relating to operations with respect to the device 40. A log is information relating to operations with respect to the device 40, and includes, for example, information indicating an operation that causes the device 40 to start operating, information including the time at which said operation was performed, and operation content of said operation. When the device 40 is a light fitting, the log includes information indicating that an operation by the user U that turns on the light fitting has been performed and the light-on time, and information indicating that the light fitting has been turned off and the light-off time, or the like. The log acquisition unit 22 is realized by the processor 12 and the communication IF 14, for example.

It should be noted that the log acquisition unit 22 may acquire a log of operations performed by the user U with respect to the information terminal apparatus 10.

The action detection unit 23 is a processing unit that detects actions performed by the user U. The action detection unit 23 detects whether or not the user U has performed an action, on the basis of the log acquired by the log acquisition unit 22. Specifically, the action detection unit 23 acquires the log from the log acquisition unit 22, and detects the performing of an operation included in the acquired log, as an action performed by the user U. Furthermore, at such time, the action detection unit 23 acquires the time at which the aforementioned operation was performed, as the time at which the user U performed the action.

The vibration data accumulation unit 24 is a processing unit that acquires the magnitude of the vibrations detected by the vibration sensor 15, namely the vibration data output by the vibration sensor 15, and accumulates and stores the acquired vibration data as vibration data 25. The vibration data accumulation unit 24 repeatedly acquires the vibration data at predetermined cycles (for example, cycles of 10 times per second). The vibration data accumulation unit 24 is realized by the processor 12 and the memory 13, for example.

The pattern learning unit 26 is a processing unit that generates a bed-leaving vibration pattern produced by the user U. The pattern learning unit 26 extracts, from among the vibration data 25 stored by the vibration data accumulation unit 24, vibration data included in a predetermined period that ends at the time at which the action detected by the action detection unit 23 was performed, and stores the vibration waveform indicated by the extracted vibration data, as a bed-leaving vibration pattern produced by the user U. The pattern learning unit 26 performs machine learning on the basis of the vibration waveforms indicated by one or more items of vibration data extracted using the aforementioned method, and generates and stores a bed-leaving vibration pattern 27 produced by the user U, on the basis of results of the machine learning. The machine learning processing can be performed using publicly known conventional technology, and can be realized by means of the "SPS Modeler" of IBM, for example.

The determination unit 28 is a processing unit that determines whether or not a vibration waveform indicated by the vibration data acquired by the vibration sensor 15 conforms with the vibration pattern 27 stored by the pattern learning unit 26. The determination unit 28 acquires vibration data from the vibration sensor 15 repeatedly at predetermined cycles (for example, cycles of 10 times per second). The determination unit 28 then uses pattern recognition processing to determine whether or not a vibration waveform indicated by the acquired vibration data conforms with the bed-leaving vibration pattern 27 of the user U stored by the pattern learning unit 26.

The determination unit 28 then controls whether or not to cause the device 40 to operate, in accordance with whether or not the vibration waveform conforms with the vibration pattern 27. Specifically, when it has been determined that the vibration waveform conforms with the bed-leaving vibration pattern 27 of the user U, control that causes the device 40 to operate is performed, and when it has been determined that the vibration waveform does not conform with the vibration pattern 27, control that causes the device 40 to operate is not performed, for example.

The device control unit 29 is a processing unit that transmits, to the device 40 via the network, a control signal that causes the device 40 to operate. The device control unit 29 transmits the control signal that causes the device 40 to operate, to the device 40, on the basis of the control performed by the determination unit 28. The device control unit 29 is realized by the processor 12 and the communication IF 14, for example.

The device 40 is an electrical device that can be controlled via the network. The device 40 receives the control signal from the information terminal apparatus 10 (the device control unit 29) via the network, and operates on the basis of the received control signal. Furthermore, the device 40 provides information relating to an operation with respect to the device 40, to the information terminal apparatus 10 (the log acquisition unit 22) via the network. The device 40 is a lighting device or a playback device that plays music or video, for example.

It should be noted that the device 40 and the information terminal apparatus 10 may be directly connected by means of a communication line, may be connected via a relay device (what is referred to as a home gateway, or the like), or may be connected via the cloud.

FIG. 5 is an explanatory diagram depicting an example of a log (a log 50) of the device 40 in the present embodiment. The log 50 depicted in FIG. 5 is an example of a log that the device 40 provides to the log acquisition unit 22.

The log 50 depicted in FIG. 5 includes information relating to operations with respect to a light fitting serving as the device 40. Specifically, the log 50 includes the items of information of a time 51 at which an operation was performed with respect to the device 40, a device name 52 that is the name of the device 40 subjected to the operation, and an operation content 53 that is the content of the operation. For example, the first log included in the log 50 indicates that an operation (turn-on operation) that turns on a "bathroom light" serving as the device 40 was performed at the time of "2:30 on Jan. 1, 2001".

Figure 6:
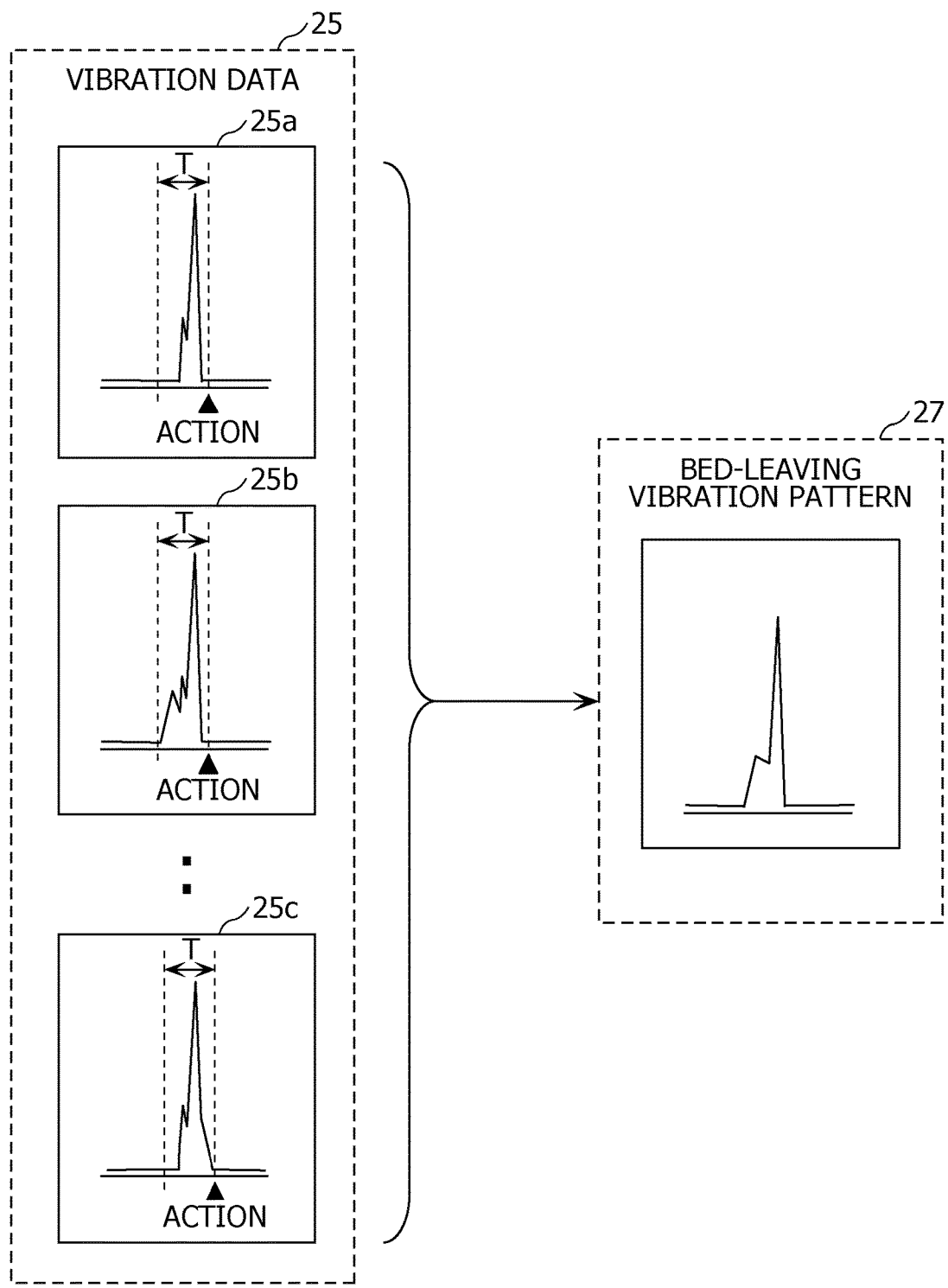
FIG. 6 is a schematic view depicting a method for generating a vibration pattern performed by a pattern learning unit in the embodiment.

FIG. 6 is a schematic view depicting a method for generating a vibration pattern performed by the pattern learning unit 26 in the present embodiment.

The vibration data 25 depicted in FIG. 6 includes vibration data 25a, 25b and 25c. Each item of the vibration data 25a, 25b . . . and 25c is vibration data of a predetermined period from among time-sequential vibration data stored by the vibration data accumulation unit 24, and has been extracted by the pattern learning unit 26. More specifically, the vibration data of the predetermined period is vibration data of a predetermined period having a time length T that ends at the time at which an action of the user U (more specifically, a light-on operation) detected by the action detection unit 23 was performed. When a plurality of times at which an action of the user U was performed have been acquired, there are also a plurality of items of vibration data extracted as mentioned above, such as the vibration data 25a, 25b, and 25c.

The pattern learning unit 26 then performs machine learning on the basis of the vibration waveforms indicated by each item of the vibration data 25a, 25b and 25c, and generates the bed-leaving vibration pattern 27 produced by the user U, on the basis of results of the machine learning. A vibration waveform is depicted as the vibration pattern 27 in FIG. 6; however, it should be noted that the vibration pattern 27 may have any form provided that the features of the vibration waveform are indicated. For example, the vibration pattern 27 may be numerical value data or a numerical formula indicating changes over time in vibration data, or a range may be designated in such a way that differences from the numerical value data or the numerical formula are within a predetermined range.

Figure 7:
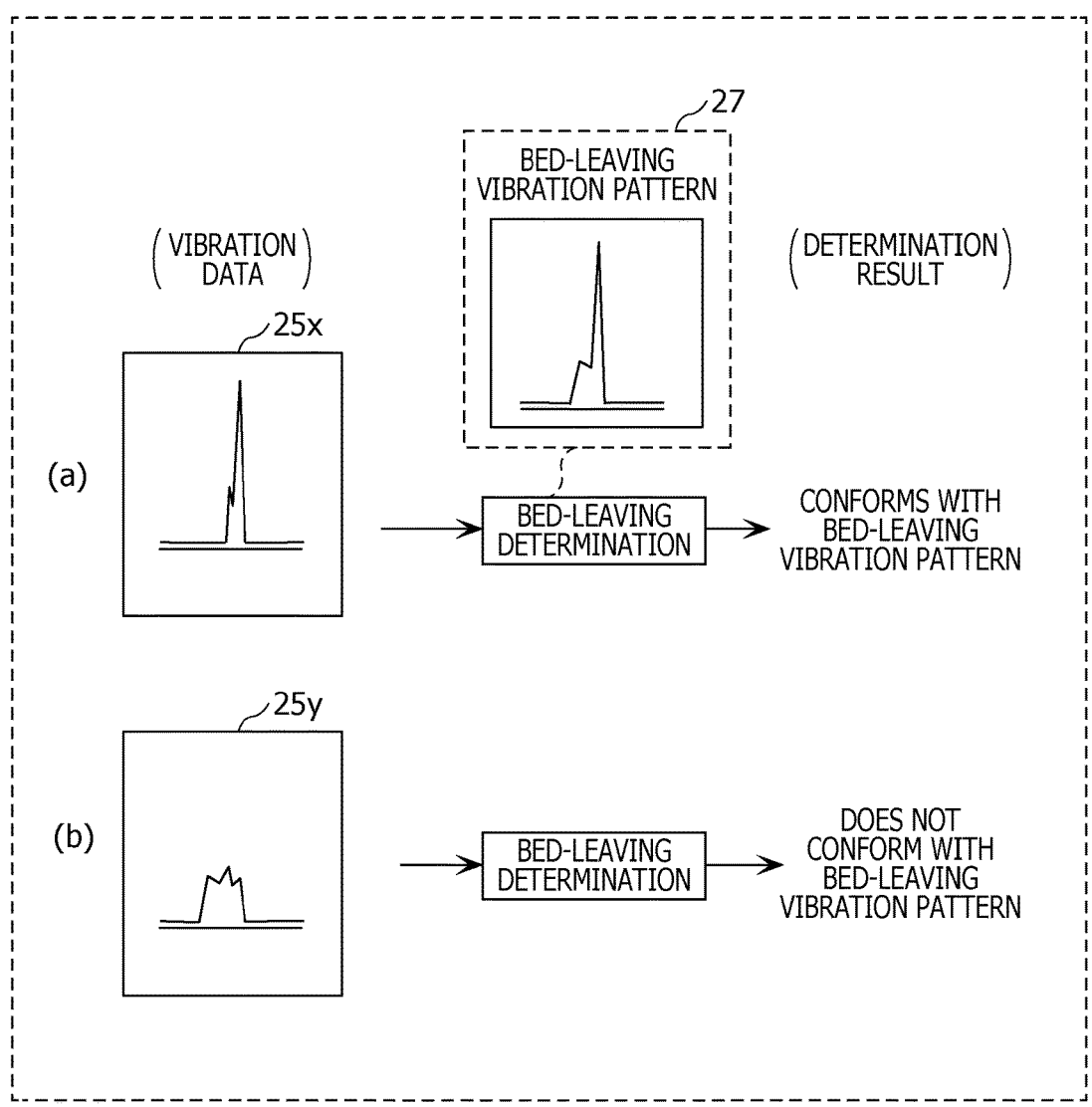
FIG. 7 is a schematic view depicting a method for determining vibration data performed by a determination unit in the embodiment.

FIG. 7 is a schematic view depicting a method for determining vibration data performed by the determination unit 28 in the present embodiment. FIGS. 7(a) and (b) respectively depict a determination method in the case where the vibration data acquired by the vibration sensor 15 has been produced by vibrations caused when the user U leaves bed, and in the case where the acquired vibration data has not been produced by vibrations caused when the user U leaves bed.

FIG. 7(a) depicts the case where it is determined that the vibration data acquired by the vibration sensor 15 has been produced by vibrations caused when the user U leaves bed. Vibration data 25x depicted in FIG. 7(a) is one item of vibration data acquired by the vibration sensor 15, and is an example of vibration data that has been produced by vibrations caused when the user U leaves bed. The determination unit 28 acquires the vibration data 25x from the vibration sensor 15, and, by means of pattern recognition processing, determines whether or not the acquired vibration data 25x conforms with the bed-leaving vibration pattern 27 of the user U. It is determined that the vibration data 25x conforms with the vibration pattern 27, in other words, that the vibration waveform indicated by the vibration data 25x has been produced by vibrations caused when the user U leaves bed.

FIG. 7(b) depicts when it is determined that the vibration data acquired by the vibration sensor 15 has not been produced by vibrations caused when the user U leaves bed. Vibration data 25y depicted in FIG. 7(b) is one item of vibration data acquired by the vibration sensor 15, and is an example of vibration data that has been produced by vibrations caused when the user U has turned over slightly in bed, and the magnitude of the vibrations is less than that of the vibration data 25x. Similar to the above, the determination unit 28 determines, by means of pattern recognition processing, whether or not the vibration data 25y conforms with the vibration pattern 27. It is determined that the vibration data 25y does not conform with the vibration pattern 27, in other words, that the vibration waveform indicated by the vibration data 25y has not been produced by vibrations caused when the user U leaves bed.

The flow of the processing performed by the information terminal apparatus 10 configured as mentioned above will be described hereinafter.

Figure 8:
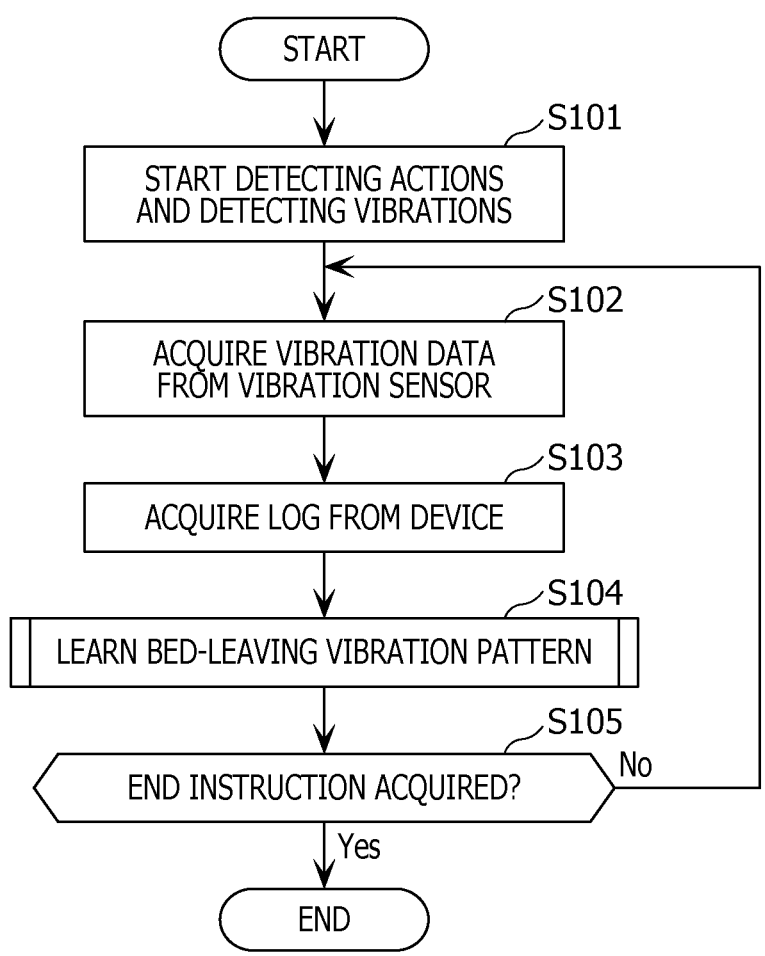
FIG. 8 is a flow diagram depicting processing from the start and to the end of body movement detection performed by the information terminal apparatus in the embodiment.

First, a series of processing from the start and to the end of body movement detection will be described. FIG. 8 is a flow diagram depicting processing from the start and to the end of the body movement detection performed by the information terminal apparatus 10 in the present embodiment.

In step S101, the state management unit 21 causes the detection of actions of the user U to be started by the action detection unit 23, and the detection of vibrations to be started by the vibration sensor 15. For example, the state management unit 21 causes the detection of actions and the detection of vibrations to be started when having received an operation for vibration pattern learning via the input IF 16.

In step S102, the vibration data accumulation unit 24 acquires vibration data from the vibration sensor 15.

In step S103, the log acquisition unit 22 acquires a log from the device 40.

In step S104, the action detection unit 23 and the pattern learning unit 26 perform learning processing with respect to the bed-leaving vibration pattern of the user U. The vibration pattern learning processing will be described in detail separately.

In step S105, the state management unit 21 determines whether or not an instruction to end action detection (an end instruction) has been received from the user U. If the end instruction has been received (yes in step S105), the series of processing depicted in FIG. 8 ends. If the end instruction has not been received (no in step S105), step S102 is executed once again.

Figure 9:
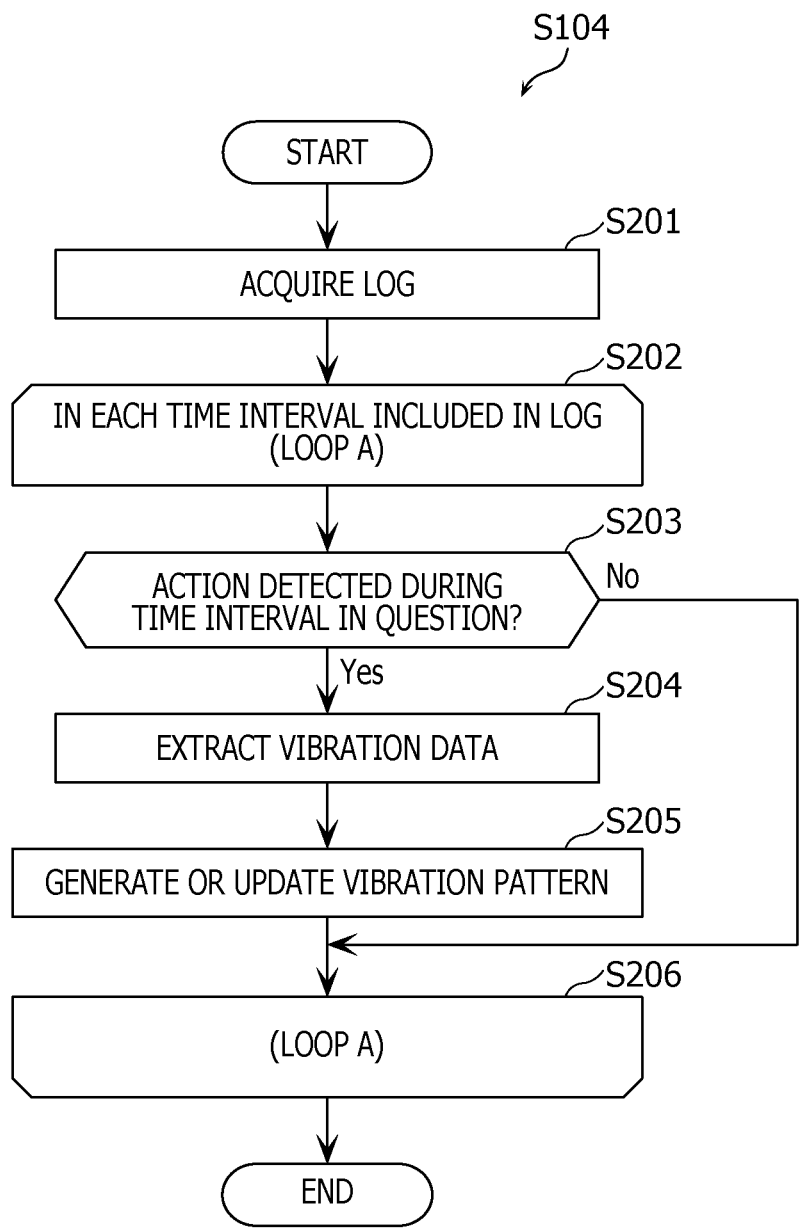
FIG. 9 is a flow diagram depicting vibration pattern learning processing performed by an action detection unit and the pattern learning unit in the embodiment.

FIG. 9 is a flow diagram depicting the vibration pattern learning processing performed by the action detection unit 23 and the pattern learning unit 26 in the present embodiment. The series of processing depicted in FIG. 9 is a detailed depiction of the processing of step S104 in FIG. 8.

In step S201, the action detection unit 23 acquires the log of the device 40 from the log acquisition unit 22.

In step S202, the action detection unit 23 and the pattern learning unit 26 perform control in such a way that the processing from step S203 to step S206 is performed, in each time interval included in the log. The length of the time interval may be arbitrarily set, and, for example, can be 1 second, 0.1 seconds, or the like.

In step S203, the action detection unit 23 attempts to detect an action of the user U in the time interval in question. Specifically, the action detection unit 23 determines whether or not the user U has performed an action in the time interval, on the basis of the log of the device 40 acquired in step S201. For example, in the case where the log of the device 40 includes information indicating that a lighting device in the bathroom was turned on in the time interval, it is determined that the user U performed an action in the time interval. If it has been determined in step S203 that there was an action in the time interval (yes in step S203), processing proceeds to step S204. However, if it has been determined that there was no action in the time interval (no in step S203), processing proceeds to step S206.

In step S204, the pattern learning unit 26 extracts, from among the vibration data possessed by the vibration data accumulation unit 24, vibration data of the predetermined period T that ends at the time at which the action detected in step S203 was performed by the user U.

In step S205, the pattern learning unit 26 generates a bed-leaving vibration pattern of the user U by means of machine learning on the basis of the vibration data extracted in step S204. It should be noted that, when a bed-leaving vibration pattern of the user U that has already been generated is possessed, the vibration pattern is updated by means of machine learning on the basis of the vibration data extracted in step S204.

In step S206, the action detection unit 23 and the pattern learning unit 26 determine whether or not the processing from step S203 to step S206 has been completed in all of the time intervals included in the log. If the aforementioned processing has been completed, the series of processing depicted in FIG. 8 ends, and if the aforementioned processing has not been completed, control is performed in such a way that the processing from step S203 to step S206 is performed for a new time interval.

As a result of the aforementioned series of processing, the information terminal apparatus 10 learns a vibration pattern for when the user U leaves bed.

Figure 10:
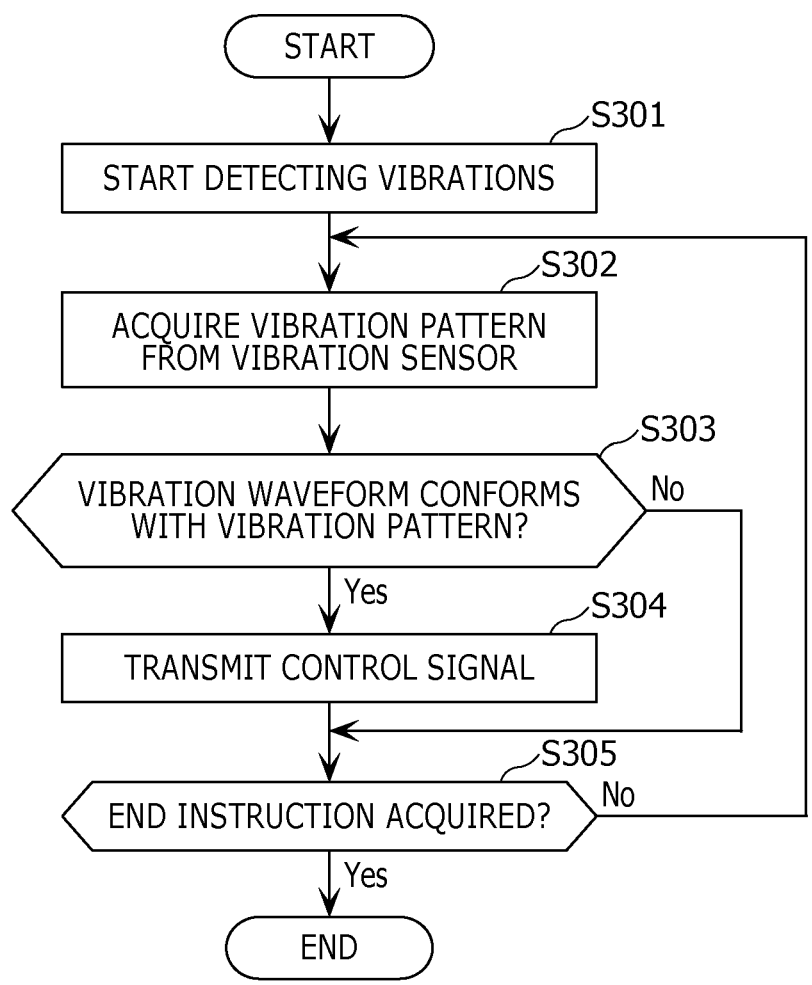
FIG. 10 is a flow diagram depicting bed-leaving determination processing performed by the determination unit in the embodiment.

Next, processing regarding determining whether the user U has left bed will be described. FIG. 10 is a flow diagram depicting bed-leaving determination processing performed by the determination unit 28 in the present embodiment.

In step S301, the state management unit 21 causes the detection of vibrations to be started by the vibration sensor 15. For example, the state management unit 21 causes the detection of vibrations to start when having received an operation for the start of the detection of vibrations via the input IF 16.

In step S302, the vibration data accumulation unit 24 acquires vibration data from the vibration sensor 15.

In step S303, the determination unit 28 determines whether or not the vibration waveform indicated by the vibration data acquired by the vibration sensor 15 in step S302 conforms with the vibration pattern 27 stored by the pattern learning unit 26. If it has been determined that the vibration waveform conforms with the vibration pattern (yes in step S303), processing proceeds to step S304. However, if it has been determined that the vibration waveform does not conform with the vibration pattern (no in step S303), processing proceeds to step S305.

In step S304, the determination unit 28 causes the device control unit 29 to transmit a control signal for controlling an operation of the device 40.

In step S305, the state management unit 21 determines whether or not an instruction to end action detection (an end instruction) has been received from the user U. If the end instruction has been received (yes in step S305), the series of processing depicted in FIG. 10 ends. If the end instruction has not been received (no in step S305), step S302 is executed once again.

As a result of the aforementioned series of processing, the information terminal apparatus 10 determines whether or not the user U has left bed, on the basis of the vibration pattern for when the user U leaves bed, generated by means of machine learning, and controls the device 40.

It should be noted that the vibration pattern for when the user U temporarily leaves bed and the vibration pattern for when the user U rises are similar but there can also be cases where these can be differentiated. This is because, in the case where the user U temporarily leaves bed, it is assumed that the user U leaves bed after there has been a comparatively short vibration, and in the case where the user U rises, it is assumed that the user U rises after a comparatively long vibration has continued due to tidying up the bedding, for example. Furthermore, even though it may not be possible to differentiate between the vibration pattern for when the user U temporarily leaves bed and the vibration pattern for when the user U rises, it is also possible to differentiate between the vibration patterns for temporarily leaving bed and rising by determining temporarily leaving bed to be a leaving-bed action that is performed a predetermined time (for example, 30 minutes) or more prior to a scheduled rising time that has been set with an alarm clock, and determining rising to be a leaving-bed action that is performed within the predetermined time (for example, 30 minutes) from the scheduled rising time.

In this way, when it is possible to differentiate between the vibration pattern for when the user U temporarily leaves bed and the vibration pattern for when the user U rises, it is also possible for the determination unit 28 to determine with which of the aforementioned vibration patterns the vibrations acquired by the vibration sensor 15 conform, and transmit mutually different control signals to the device 40, or transmit control signals to different devices 40, in accordance with which of the aforementioned vibration patterns the vibrations conform.

It should be noted that the aforementioned explanation describes a method with which a bed-leaving vibration pattern of the user U is generated by means of machine learning, and the generated vibration pattern is used as a basis to detect the user U leaving bed. It is also possible for a bed-entering vibration pattern of the user U to be generated by means of machine learning with a method that is similar to the aforementioned.

Figure 11:
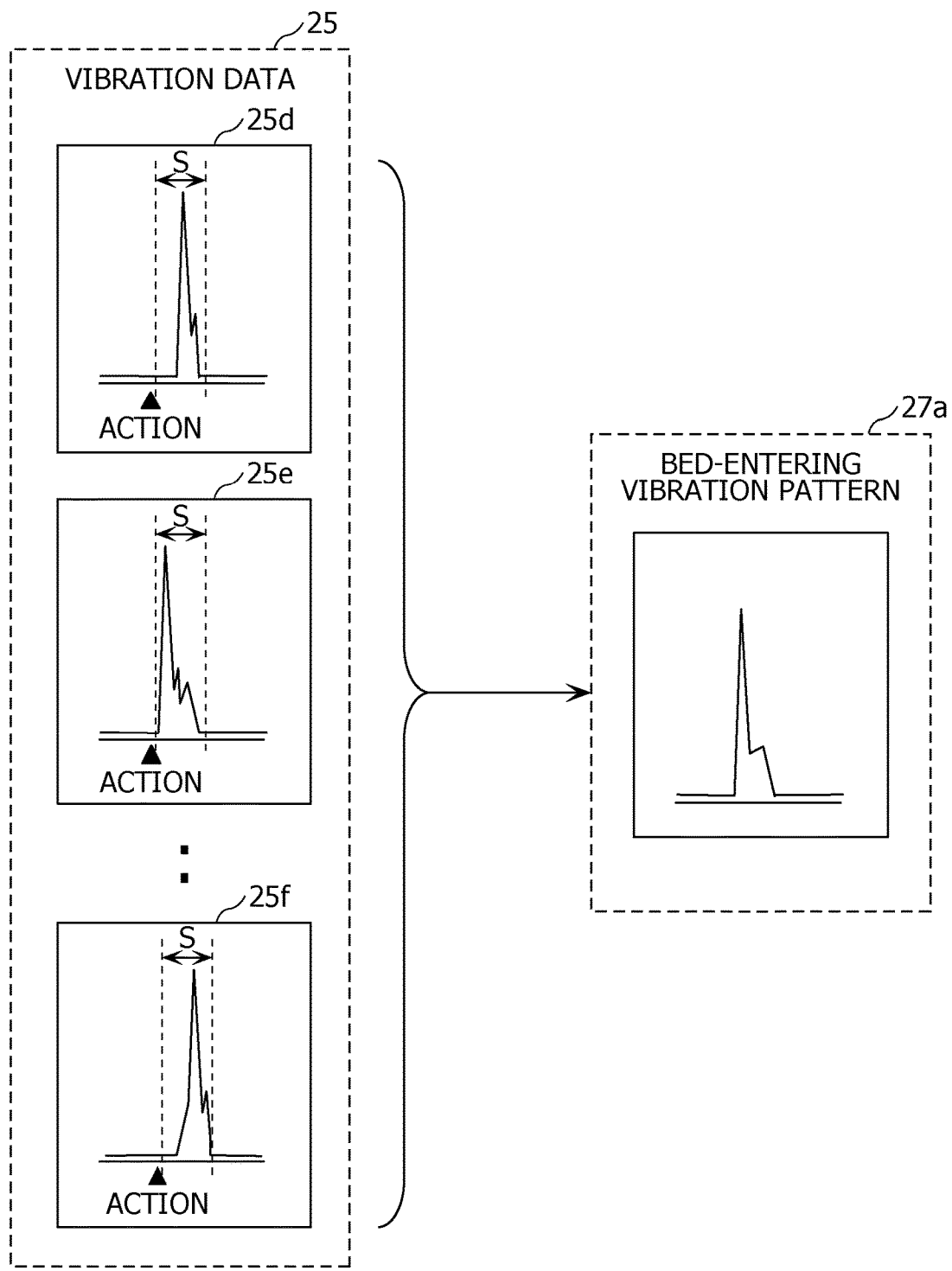
FIG. 11 is a schematic view depicting a method for generating a bed-entering vibration pattern performed by the pattern learning unit in the embodiment.

FIG. 11 is a schematic view depicting a method for generating a bed-entering vibration pattern performed by the pattern learning unit 26 in the present embodiment. The method for generating a bed-entering vibration pattern is similar to the method for generating a bed-leaving vibration pattern depicted in FIG. 6, except that the method for setting the predetermined period is different. In other words, the action detection unit 23 detects a light-off operation performed by the user U, as an action of the user U. The pattern learning unit 26 then extracts, from among time-sequential vibration data stored by the vibration data accumulation unit 24, vibration data 25d, 25e . . . and 25f of a predetermined period having a time length S that starts at the time at which the aforementioned action of the user U was performed, and generates a bed-entering vibration pattern 27a by means of machine learning.

In this case, the determination unit 28 determines whether or not a vibration waveform indicated by the vibration data acquired by the vibration sensor 15 conforms with the bed-leaving vibration pattern 27 of the user U, and also determines whether or not said vibration data conforms with the bed-entering vibration pattern 27a of the user U. Different control can then be performed (or not performed) with respect to the device 40 when it has been determined that the vibration waveform conforms with the bed-leaving vibration pattern 27, when it has been determined that the vibration waveform conforms with the bed-entering vibration pattern 27a, or when it has been determined that the vibration waveform does not conform with either of the aforementioned vibration patterns.

An explanation will be given regarding an example of control of the device 40 that becomes possible by applying the processing for determining a bed-leaving vibration pattern, the differentiation between the vibration pattern for when the user U temporarily leaves bed and the vibration pattern for when the user U rises, and the processing for determining the bed-entering vibration pattern described above.

Figure 12:
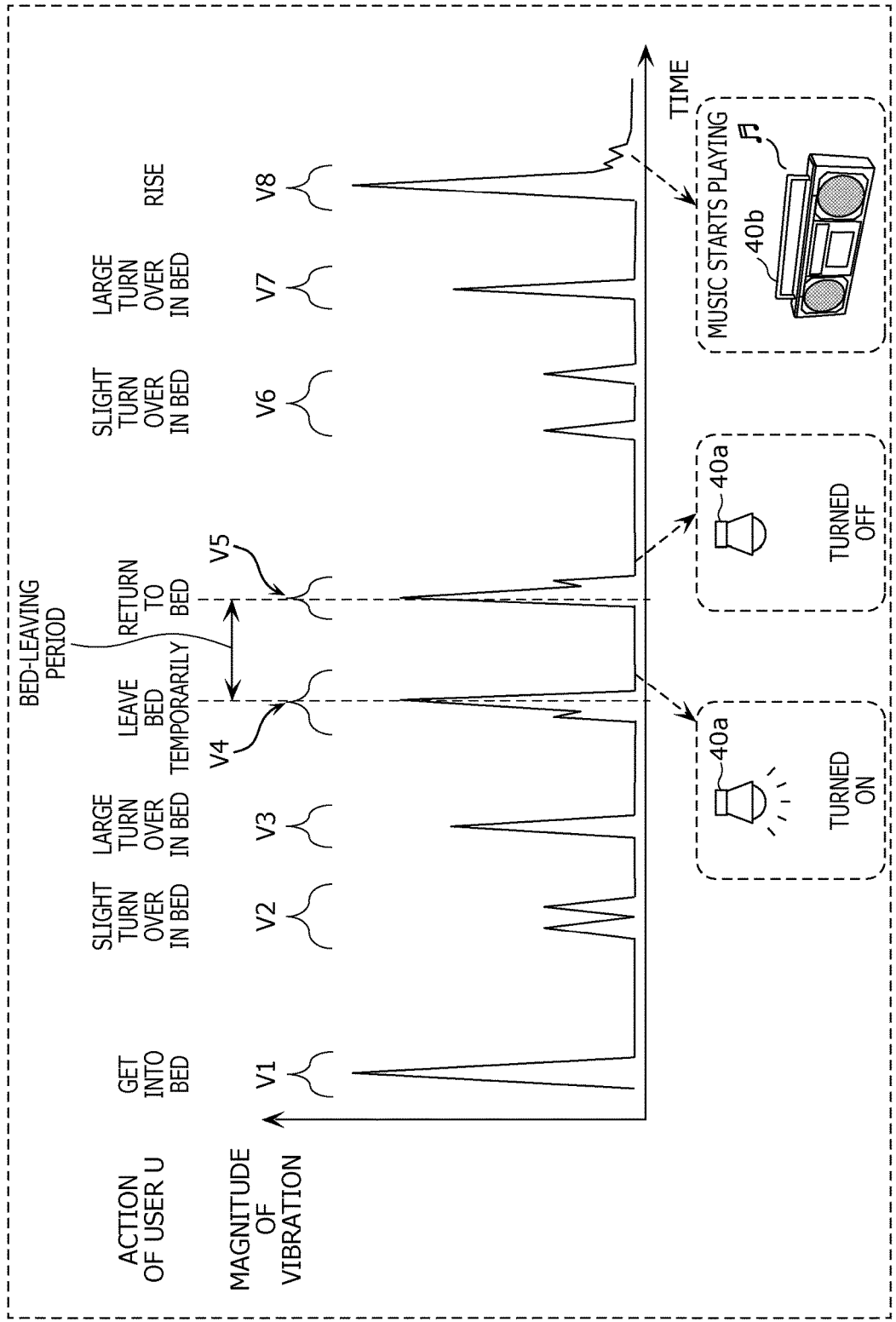
FIG. 12 is an explanatory diagram depicting the magnitude of vibrations detected by the information terminal apparatus and an example of device control in the embodiment.

FIG. 12 is an explanatory diagram depicting the magnitude of vibrations detected by the information terminal apparatus 10 and an example of device control in the present embodiment.

A lighting device 40a and a music player 40b depicted in FIG. 12 are examples of the device 40. The information terminal apparatus 10 performs processing for determining bed-leaving vibration patterns, and thereby controls the device 40 when the user U temporarily leaves bed and when the user U rises. Furthermore, the information terminal apparatus 10 is able to differentiate between when the user U temporarily leaves bed and when the user U rises. By applying this, for example, it is possible to expect the effects of suppression of an increase in the feeling of awakening, by the lighting device 40a being turned on in a predetermined lighting mode (for example, dimmed lighting) when the user U temporarily leaves bed, and elimination of uneasiness caused by silence, by predetermined music or a sound (for example, a natural sound) being played using the music player 40b. Furthermore, it is possible to expect the effects of increasing the feeling of awakening by the lighting device 40a being turned on in a predetermined lighting mode that is different from the aforementioned lighting mode (for example, full lighting) when the user U rises, and a refreshed awakening for the user U being stimulated by music that is different from the aforementioned music or sound (for example, invigorating music) being played using the music player 40b.

The information terminal apparatus 10, by performing processing for determining a bed-entering vibration pattern, is able to perform control with which the lighting device 40a is turned off after the user U gets into bed.

It should be noted that the device 40 may be a device having the purpose of detecting the actions of the user U (for example, a person-detecting sensor or an infra-red camera), or the like. In such a case, the action detection unit 23 acquires the time at which the person-detecting sensor or the like has detected the user U, as the time of an action performed by the user U.

(Modified Example of Embodiment)

In the present modified example, a body movement measuring system that determines movements of a user with greater precision will be described. In the body movement measuring system in the present modified example, the functions of the information terminal apparatus in the embodiment are realized by the information terminal apparatus and a server operating in a cooperative manner.

Figure 13:
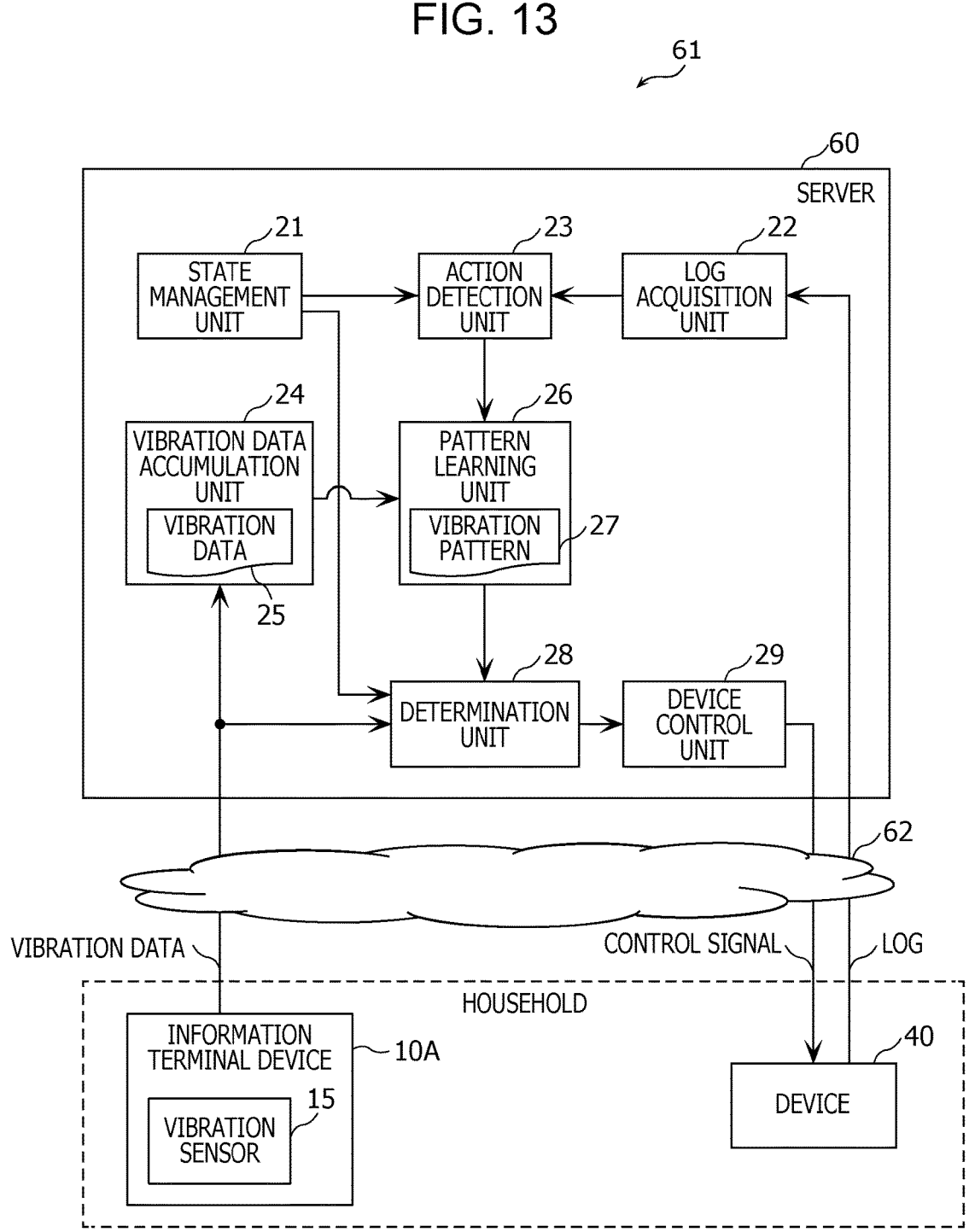
FIG. 13 is a block diagram depicting a functional configuration of a body movement measuring system in a modified example of the embodiment.

FIG. 13 is a block diagram depicting a functional configuration of a body movement measuring system 61 in the present modified example.

As depicted in FIG. 13, the body movement measuring system 61 in the present modified example is provided with an information terminal apparatus 10A and a server 60. The information terminal apparatus 10A and the server 60 are communicably connected via a network 62. The network 62 is the Internet, for example, and may include a local area network (LAN), a mobile telephone line, or the like.

The information terminal apparatus 10A is provided with at least the vibration sensor 15, and is communicably connected to the vibration data accumulation unit 24 and the determination unit 28 of the server 60 via the network 62. Vibration data acquired by the vibration sensor 15 is provided to the vibration data accumulation unit 24 and the determination unit 28 via the network 62.

The server 60 is provided with functional blocks for the functions provided in the information terminal apparatus 10 such as the state management unit 21, except for the vibration sensor 15. The device control unit 29 of the server 60 transmits a control signal to the device 40 via the network 62, and the log acquisition unit 22 acquires a log from the device 40 via the network 62. The server 60 may be realized by means of what is referred to as a cloud server, and may be arranged anywhere physically or geographically as long as the server 60 is communicably connected to the information terminal apparatus 10A and the device 40 via the network 62.

The same functions as those of the information terminal apparatus 10 in the embodiment are realized by the body movement measuring system 61. In addition, since the main storage units and processing units such as the action detection unit 23, the vibration data accumulation unit 24, the pattern learning unit 26, and the determination unit 28 are realized in the server 60, there is an advantage in that data management, software updating, and the like can be realized more safely and easily.

It should be noted that, generally, a cloud server has the advantage of reducing introduction and maintenance operation costs for hardware and software, for example. Thus, the body movement measuring system 61 is able to benefit from the advantages of a cloud server.

As mentioned above, the information terminal apparatus of the present embodiment generates a bed-leaving vibration pattern on the basis of body movements of the user in bedding actually being used by the user in a predetermined period before the time at which the user performed an action. In this way, because the vibration pattern is generated on the basis of vibrations in the bedding actually being used, it is possible to more precisely determine a body movement of the user in this bedding, using this generated vibration pattern. Thus, the information terminal apparatus is able to determine movements of the user with greater precision.

Furthermore, the information terminal apparatus is able to control an electrical device when having determined that the user has left bed on the basis of the generated vibration pattern. Thus, when the user has left bed, it is possible for the information terminal apparatus to determine that the user has left bed and automatically control the electrical device, thereby improving convenience.

The information terminal apparatus generates a bed-leaving vibration pattern of the user with the time at which the user operated the electrical device serving as the time at which the user performed an action. In this way, the information terminal apparatus is able to specifically determine movements of the user with greater precision.

The information terminal apparatus generates a bed-leaving vibration pattern of the user with the time at which the user operated the information terminal apparatus serving as the time at which the user performed an action. In this way, the information terminal apparatus is able to specifically determine movements of the user with greater precision.

The information terminal apparatus generates a bed-leaving vibration pattern of the user with the time at which the user was detected by a person-detecting sensor serving as the time at which the user performed an action. In this way, the information terminal apparatus is able to specifically determine movements of the user with greater precision.

The information terminal apparatus generates a bed-leaving vibration pattern of the user by means of machine learning. In this way, the information terminal apparatus generates the vibration pattern by means of machine learning on the basis of vibrations in the bedding actually being used, and is therefore able to more precisely determine a body movement of the user in this bedding.

The information terminal apparatus no longer performs machine learning when a vibration pattern learning period has ended, and therefore there is an advantage in that the processing load is reduced.

It should be noted that, in the aforementioned embodiments, the constituent elements may be configured by using dedicated hardware, or may be realized by executing a software program suitable for the constituent elements. The constituent elements may be realized by a program execution unit such as a CPU or a processor reading out and executing a software program recorded in a recording medium such as a hard disk or a semiconductor memory. Here, software that realizes the information terminal apparatus and the like of the aforementioned embodiments is a program such as the following.

More specifically, this program causes a computer to execute operations including: acquiring, using a vibration sensor of the information terminal apparatus, vibration data that is time-sequential data of vibrations, including vibrations based upon body movements of a user on bedding on which the information terminal apparatus is placed; storing the acquired vibration data in a memory of the information terminal apparatus; detecting an action performed by the user; and extracting, from among the vibration data stored in the memory, vibration data included in a predetermined period that ends at a time at which the detected action was performed, and storing a vibration waveform indicated by the extracted vibration data, in the memory as a bed-leaving vibration pattern produced by the user.

An information terminal apparatus and the like according to one or more aspects has been described above on the basis of the embodiments; however, the present disclosure is not restricted to these embodiments. Modes in which various modifications conceived by a person skilled in the art have been implemented in the present embodiments, and modes constructed by combining the constituent elements in different embodiments may also be included within the scope of one or more aspects provided they do not depart from the purpose of the present disclosure.

The present disclosure can be used for a body movement measuring apparatus that measures body movements, a control device that controls another device on the basis of the detection of body movements, and the like.

What is claimed is:

1. A method comprising:
acquiring, using a vibration sensor of an information terminal apparatus, vibration data (i) that is time-sequential vibration data and (ii) that includes information on vibrations by body movements of a user on bedding on which the information terminal apparatus is placed;
storing the acquired vibration data in a memory of the information terminal apparatus;
detecting an action performed by the user;
extracting, from among the stored vibration data, vibration data included in a predetermined period that ends at a time at which the detected action was performed, and storing a vibration waveform indicated by the extracted vibration data, in the memory as a bed-leaving vibration pattern produced by the user;
determining whether or not the vibration waveform indicated by the acquired vibration data conforms with the vibration pattern stored in the memory; and
when the vibration waveform indicated by the acquired vibration data is determined to conform with the vibration pattern, transmitting, via a network, a control signal that causes operation of an electrical device that is controlled by the information terminal apparatus.

2. The method according to claim 1, wherein,
the electrical device is a lighting equipment,
the control signal causes the lighting equipment to turn on a light.

3. The method according to claim 1, further comprising:
acquiring log information that includes a time at which an operation by the user was performed with respect to the electrical device,
wherein,
when the action performed by the user is to be detected, the action performed by the user is detected using the acquired log information, and,
when the vibration pattern is to be stored in the memory, the vibration pattern is stored in the memory with the time included in the acquired log information, being used as the time at which the action was performed.

4. The method according to claim 1, further comprising:
acquiring log information that includes a time at which an operation by the user was performed with respect to the information terminal apparatus,
wherein,
when the action performed by the user is to be detected, the action performed by the user is detected using the acquired log information, and,
when the vibration pattern is to be stored in the memory, the vibration pattern is stored in the memory with the time included in the acquired log information, being used as the time at which the action was performed.

5. The method according to claim 1, further comprising:
acquiring a detection result produced by a person-detecting sensor capable of detecting that the user is in a location that is different from on the bedding,
wherein,
when the action performed by the user is to be detected, the action performed by the user is detected using the acquired detection result, and,
when the vibration pattern is to be stored in the memory, the vibration pattern is stored in the memory with a time included in the acquired detection result, being used as the time at which the action was performed.

6. The method according to claim 1, wherein,
when the vibration pattern is to be stored in the memory, the vibration pattern is generated by machine learning with the vibration waveform indicated by the extracted vibration data serving as teacher data, and the generated vibration pattern is stored in the memory.

7. The method according to claim 6, wherein generation of the vibration pattern by machine learning is performed only in a period determined as being a period in which a vibration pattern using the body movements of the user is to be learned.

8. A body movement measuring apparatus, comprising:
a vibration sensor capable of detecting vibrations of the body movement measuring apparatus;
a memory;
a processor; and
a medium having a computer program stored thereon, the computer program causing the processor to execute operations including:
  acquiring vibration data (i) that is time-sequential data of the vibrations detected by the vibration sensor and (ii) that includes information on vibrations by body movements of a user on bedding on which the body movement measuring apparatus is placed, and storing the acquired vibration data in the memory;
  detecting an action performed by the user;
  extracting, from among the vibration data stored in the memory, vibration data included in a predetermined period that ends at a time at which the detected action was performed, and storing a vibration waveform indicated by the extracted vibration data, in the memory as a bed-leaving vibration pattern produced by the user;
  determining whether or not the vibration waveform indicated by the acquired vibration data conforms with the vibration pattern stored in the memory; and
  when the vibration waveform indicated by the acquired vibration data is determined to conform with the vibration pattern, transmitting, via a network, a control signal that causes operation of an electrical device that is controlled by the information terminal apparatus.

9. A non-transitory recording medium having a computer program stored thereon, the computer program causing a processor of an information terminal apparatus to execute operations comprising:
  acquiring, using a vibration sensor of the information terminal apparatus, vibration data (i) that is time-sequential data of vibrations and (ii) that includes vibrations by body movements of a user on bedding on which the information terminal apparatus is placed;
  storing the acquired vibration data in a memory of the information terminal apparatus;
  detecting an action performed by the user;
  extracting, from among the vibration data stored in the memory, vibration data included in a predetermined period that ends at a time at which the detected action was performed, and storing a vibration waveform indicated by the extracted vibration data, in the memory as a bed-leaving vibration pattern produced by the user;
  determining whether or not the vibration waveform indicated by the acquired vibration data conforms with the vibration pattern stored in the memory; and
  when the vibration waveform indicated by the acquired vibration data is determined to conform with the vibration pattern, transmitting, via a network, a control signal that causes operation of an electrical device that is controlled by the information terminal apparatus.

* * * * *